(12) United States Patent
Nakaichi et al.

(10) Patent No.: US 6,432,043 B2
(45) Date of Patent: Aug. 13, 2002

(54) ENDOSCOPE

(75) Inventors: Katsumi Nakaichi; Shinji Yamamori; Noriaki Todokoro, all of Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/907,822

(22) Filed: Jul. 19, 2001

(30) Foreign Application Priority Data

Jul. 19, 2000 (JP) ........................................ 2000-219804

(51) Int. Cl.[7] .............................................. A61B 1/008
(52) U.S. Cl. ...................... 600/120; 600/146; 600/150; 600/194
(58) Field of Search ................................. 600/120, 188, 600/194, 199, 150, 146; 604/95.04, 510, 528

(56) References Cited

U.S. PATENT DOCUMENTS 5,135,517 A  8/1992  McCoy ........................ 604/281
5,683,348 A  11/1997  Diener ........................ 600/143
5,941,816 A  8/1999  Barthel et al. .............. 600/120

*Primary Examiner*—John Mulcahy
(74) *Attorney, Agent, or Firm*—Sughrue Mion, PLLC

(57) ABSTRACT

An endoscope for endotracheal intubation includes an elongated insertion section having a handle operation section, a bending operation mechanism and a bending mechanism for bending the insertion section, the bending mechanism including a long elastic member having one end positioned near the distal end portion of the insertion section and the other end fixedly coupled to the bending operation mechanism, a push-pull member having one end positioned near the distal end portion of the insertion section and the other end connected to the bending mechanism, a hollow member for coupling together distal end portions of the elastic member and the push-pull member so as to cause the portions to oppose each other along a bending direction, wherein the distal end portions of the elastic member and the push-pull member, which are coupled together with the hollow member, are provided integrally so as to provide a free end.

5 Claims, 4 Drawing Sheets

NATURAL STATE

BENT STATE

RESTORE BY EXTERNAL FORCE

ENDOSCOPE

BACKGROUND OF INVENTION

1. Field of Invention

The present invention relates to an endoscope for intubating an endotracheal tube, the endoscope enabling optical observation of a patient's body cavity so that an operator can easily intubate the endotracheal tube into a patient when the patient experiences difficulty in breathing because of a sudden onset of disease or an injury at the scene of an accident, disaster, or a like occurrence and the patient's airway must be ensured urgently. More specifically, the present invention relates to the bending mechanism of an operation section of an endoscope for intubating an endotracheal tube.

2. Field of Invention

As described in Unexamined Japanese Patent Publication 2000-116595, there has already been conceived a related-art bending mechanism of an endoscope for intubating an endotracheal tube. This mechanism is provided with a long elastic sheet member. A distal end portion of the sheet member is held as a free end in the vicinity of a distal end of an insertion section, and a proximal end of the sheet member is fixed to a handle operation section. A push-pull member consisting of a long sheet or wire is provided so as to extend along the elastic sheet member. A distal end portion of the push-pull member is connected to the distal end portion of the elastic sheet member. A proximal end of the push-pull member is connected to a bending operation mechanism provided in the handle operation section. When the push-pull member is pulled, the bending mechanism is bent.

A distal end portion of the bending mechanism is free or movable with respect to the construction of a distal end portion of an endoscope. Hence, when the bending mechanism is bent by pulling the push-pull member toward the handle operation section, the resultant compression force is not exerted on the distal end portion of the endoscope. Accordingly, there is yielded an advantage of the endoscope being able to bend without involvement of a reduction in the length of the endoscope. Another advantage of the bending mechanism lies in that use of a sheet enables stable bending of the endoscope in a certain direction without involvement of a twist in the bending mechanism. However, if an attempt is made to strain the bending mechanism so as to recover from a bent state, the elastic sheet member is apt to snap.

Such snapping arises because of the following reasons.

FIGS. 3(a) to (d) show variations in a related-art bending mechanism at the time of bending operation.

In a natural state, the length of the elastic sheet member 109 from its distal end to a reference position E is set to D such that the elastic sheet member 109 is free of bending, wherein the reference position E is fixed relatively to the handle operation section. Similarly, in a natural state, the length of the push-pull member 110 from its distal end to the reference position E is set to A such that the push-pull member 110 is free of bending. When the bending mechanism is bent, the push-pull member 110 is pulled by the bending operation mechanism. As a result, the length A of the push-pull member 110 from its distal end to the reference position E is shortened to B. In contrast, the length D of the elastic sheet member 109 from its distal end to the reference position E remains unchanged. Hence, the elastic sheet member 109 is bent by only the amount corresponding to a difference between the lengths A and B. If an attempt is made to forcefully restore the bending mechanism from a bent state by external force, the portion of the push-pull member 110 extending from the distal end to the reference position E attempts to become straight while the push-pull member 110 continues to be the length B. At this time, the elastic sheet member 109 also attempts to become straight. However, the length of the elastic sheet member 109 from its distal end to the reference position E is longer than the push-pull member 110 by only the difference between the lengths A and B, and hence the elastic sheet member 109 attempts to absorb the difference by meandering. At this time, the push-pull member 110 remains in a stiff state, and hence the elastic sheet member 109 cannot jut out toward the push-pull member 110, but can jut out in only the opposite direction of the push-pull member 110. Since the elastic sheet member 109 juts out in only one side thereof, the resultant flexion is subjected to strong bending. Hence, the elastic sheet member 109 is apt to snap.

SUMMARY OF INVENTION

The present invention has been conceived to solve the problem set forth and is aimed at providing a bending mechanism which prevents shortening of an endoscope, which would otherwise be caused by compression force when the force is exerted to bend the endoscope, and which obviates the risk of occurrence of snapping in an elastic sheet member while a bending mechanism maintains its performance of stably causing a bending in a certain direction.

The present invention is also aimed at providing a bending mechanism which effectively utilizes an inner cavity of an insertion section of an endoscope and accomplishes the above-described object by minimizing the outer diameter of the insertion section.

An endoscope for intubating an endotracheal tube according to the present invention comprising:

An endoscope for intubating an endotracheal tube comprising:
- an elongated insertion section having at least an image-transmitting fiber bundle and an illumination-light-transmitting fiber bundle;
- a handle operation section coupled to a proximal end of the insertion section;
- a bending operation mechanism provided in the handle operation section; and
- a bending mechanism for bending the insertion section provided so as to extend from the inside of the insertion section to the bending operation mechanism, the bending mechanism including:
  - a long elastic member having one end positioned in the vicinity of the distal end portion of the insertion section and the other end fixedly coupled to the proximal end portion of the insertion section or the handle operation section;
  - a push-pull member having one end positioned in the vicinity of the distal end portion of the insertion section and the other end connected to the bending operation mechanism;
  - a hollow member for coupling together a distal end portion of the elastic member and a distal end portion of the push-pull member so as to cause the portions to oppose each other along a bending direction,
  - wherein the distal end portion of the elastic member and the distal end portion of the push-pull member, which are coupled together with the hollow member, are provided integrally so as to provide a free end.

Preferably, the elastic member is formed of a sheet, and the push-pull member is formed of a sheet.

Further, the hollow member is preferably embodied in an annular member.

Also, the hollow member, the elastic member and the push-pull member are formed integrally.

In the bending mechanism of the endoscope according to the present invention, the distal end portion of the elastic member and the distal end portion of the push-pull member are coupled together with a hollow member while they are made to oppose each other along a bending direction. The distal end portion of the elastic member and the distal end portion of the push-pull member coupled with the hollow member are provided integrally as a single uniform free end which is not fixed, directly or indirectly, to another distal end constituent element. Even when the push-pull member is pulled so as to bend the bending mechanism, compression force does not act on the distal end constituent section. Hence, the insertion section is not shortened. The elastic member and the push-pull member are coupled with the hollow member while being opposed to each other along a bending direction. As a result, the elastic member and the push-pull member are spaced apart from each other and do not compete with each other, which would otherwise be the case when the bending mechanism is restored from a bending state or a bent state by external force. The elastic member can meander without being limited by the push-pull member, and hence bending can be concentrated in a certain direction, thereby eliminating the risk of the elastic member being snapped.

Preferably, the elastic member is formed of a sheet. As a result, even when the insertion section of the endoscope attempts to twist when the bending mechanism is bent, the sheet is easily bent in a thicknesswise direction thereof but is bent in a widthwise direction thereof with difficulty. Hence, the elastic member provides resistance to twisting action of the elastic member in the bending direction. Hence, stable bending action of the bending mechanism in the bending direction is ensured.

Further, the push-pull member is formed of a sheet, or the elastic member and the push-pull member are formed of sheets. As mentioned above, a more stable bending direction is maintained.

The distal end portion of the elastic member and the distal end portion of the push-pull member are coupled together with a hollow member while they are made to oppose each other along a bending direction. As a result, a space in the center of the hollow member can be ensured. An image-transmitting fiber bundle and an illumination-light-transmitting fiber bundle can be efficiently passed into the space. Further, the hollow member is formed of an annular member. Since the internal space of the insertion section usually assumes a circular cross section, the internal space can be utilized effectively. Therefore, there is obviated a necessity of undesirably increasing the diameter of the insertion, and hence the insertion section can be made narrow.

Further, the hollow member, the elastic member and the push-pull member may be formed integrally .

DETAILED DESCRIPTION OF PREFERRED EMBODIMENTS

An embodiment of the present invention will be described hereinbelow by reference to the accompanying drawings.

Figure 1:
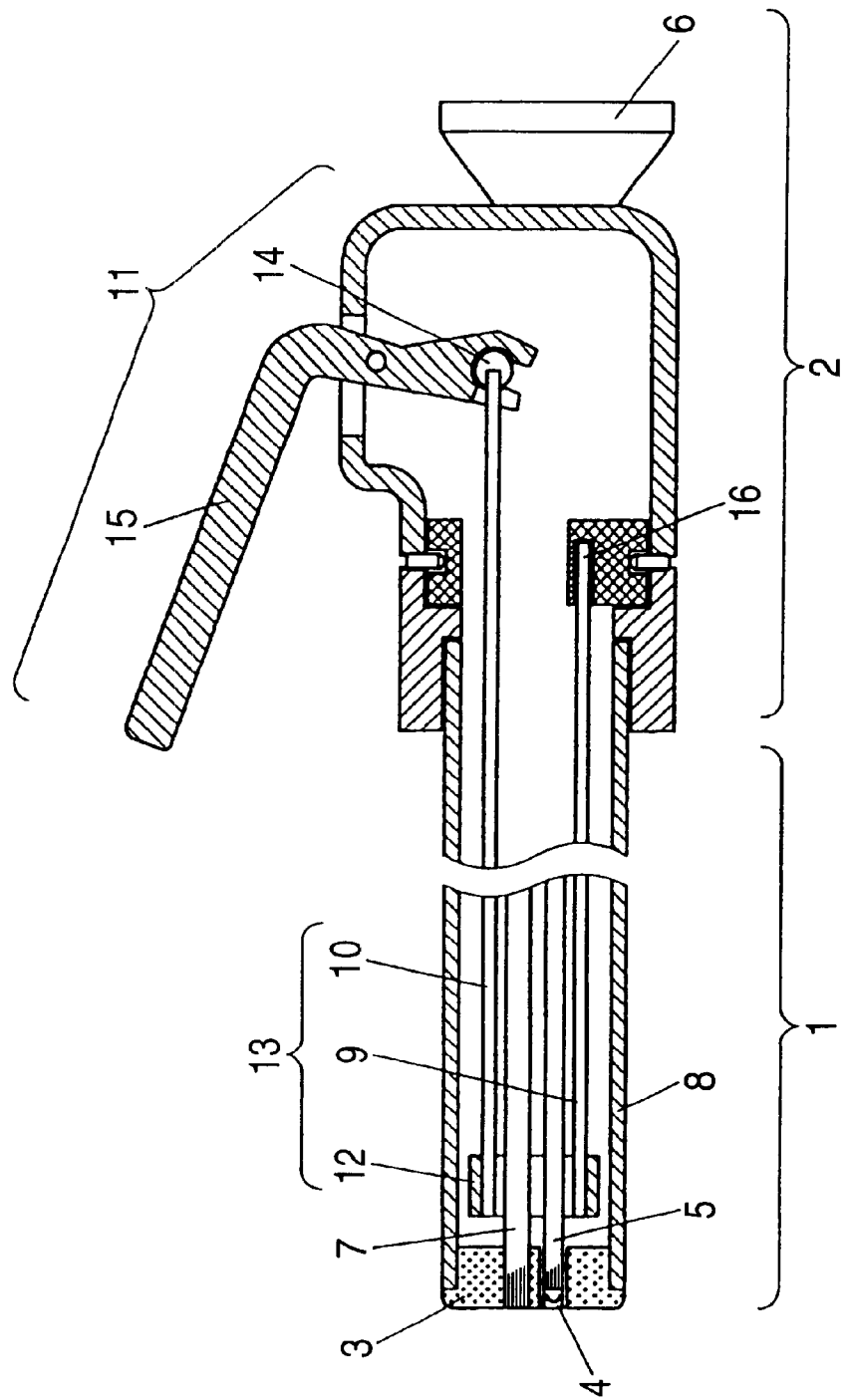
FIG. 1 is a general view showing the construction of an endoscope for intubating an endotracheal tube according to an embodiment of the present invention.

FIG. 1 is a general view showing the construction of an endoscope for intubating an endotracheal tube according to the embodiment of the present invention.

The endoscope for intubating an endotracheal tube according to the present invention comprises an insertion section 1 to be inserted into an inner cavity of the endotracheal tube, and a handle operation section 2 which is connected to a proximal end side of the insertion section 1 and is disposed outside the endotracheal tube.

The insertion section 1 has an elongated shape. A distal end portion 3 is provided at the distal end portion of the insertion section 1, and an objective lens 4 is provided in an end face of the distal end portion 3. A distal end of an image-transmitting fiber bundle 5 is optically coupled to the objective lens 4. The image-transmitting fiber bundle 5 is led to the handle operation section 2 through the inner cavity of the insertion section 1. The other end of the image-transmitting fiber bundle 5 is optically coupled to an eye-piece portion 6 provided in the handle operation section 2 (omitted from FIG. 1). Adistal end of an illumination-light-transmitting fiber bundle 7 consisting of one or a plurality of fibers is opened in the neighborhood of the objective lens 4 located at the distal endportion 3. The other end of the illumination-light-transmitting fiber bundle 7 is optically coupled to an unillustrated light source portion provided in the handle operation section 2. Here, the illumination-light-transmitting fiber bundle 7 may be disposed so as to surround the objective lens 4. The light source portion of the illumination-light-transmitting fiber bundle 7 is electrically connected to an unillustrated power supply portion provided in the handle operation section 2 and is supplied with power.

The portion of the endoscope between the distal end portion 3 of the insertion section 1 and the proximal end portion of the same is sheathed with a plastic tube 8.

The insertion section 1 incorporates an elastic sheet member 9 formed of elastic metal; e.g., stainless steel, and a push-pull sheet member 10 formed of elastic metal; e.g., stainless steel.

A distal end portion of the elastic member 9 extends to the neighborhood of the distal end portion 3, and a proximal end portion of the elastic member 9 is fastened to the handle operation section 1 so as to constitute a stationary end 16. A distal end portion of the push-pull member 10 extends in vicinity of the distal end portion 3 of the insertion section 1, and a proximal end portion of the push-pull member 10 is coupled to a bending operation mechanism 11 provided in the handle operation section 2.

A hollow annular member 12 is fitted around the distal end portion of the elastic member 9 and the distal end portion of the push-pull member 10. The distal end portion of the elastic member 9 and the distal end portion of the push-pull member 10 are connected to an inner side surface of the annular member 12 so as to oppose each other in a bending direction.

The elastic member 9, the push-pull member 10, and the annular member 12 constitute a bending mechanism 13. The distal end portion of the elastic member 9, the distal end portion of the push-pull member 10, and the annular member 12 are not fastened either to the distal end portion 3 of the insertion section 1 or to the plastic tube 8, thus constituting free ends.

Rather than being fixed on the handle operation section 2, the proximal end portion of the elastic member 9 may be fixed on a proximal end portion of the insertion section 1.

Rather than assuming the form of a sheet, the push-pull member 10 may be a wire. Further, the elastic member 9 and the push-pull member 10 may be made of resin rather than of metal.

Figure 4:
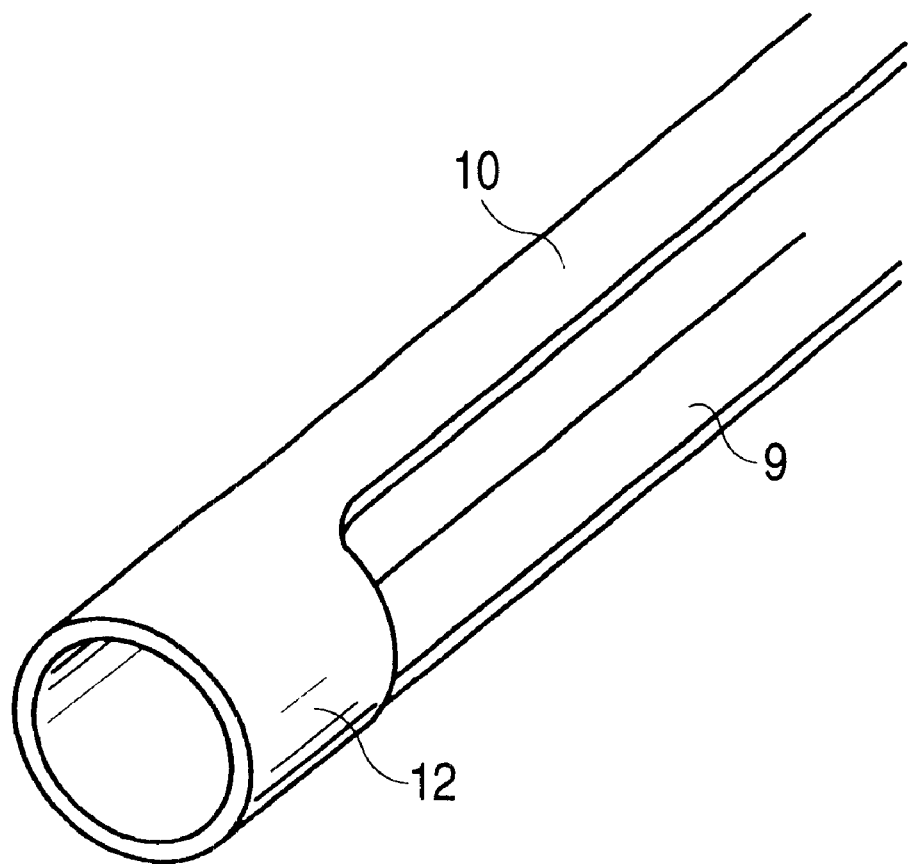
FIG. 4 is showing another embodiment of a bending mechanism of the present invention.

Rather than being connected to the inner side surface of the annular member 12, the elastic member 9 and the push-pull member 10 may be connected to an external side surface of the same. Alternatively, as shown in FIG. 4, the elastic member 9, the push-pull member 10, and the annular member 12 may be formed into one piece.

The push-pull member 10 is connected to the bending operation mechanism 11 by a terminal 14 secured on the end of the push-pull member 10. The terminal 14 is engaged with a lever 15 of the bending operation mechanism 11 such that the terminal 14 is pulled toward the eyepiece portion 6 when the lever 15 is pushed on.

The image-transmitting fiber bundle 5 and the illumination-light-transmitting fiber bundle 7 provided in the insertion section 1 are provided between the elastic member 9 and the push-pull member 10 and are led to the distal end portion 3 so as to pass through the inside of the annular member 12.

At the time of use of the endoscope having the foregoing construction, the insertion section 1 of the endoscope is first inserted into the inner cavity of the endotracheal tube. The insertion section 1 and the endotracheal tube are fixedly connected together and adjusted such that the distal end portion of the endoscope is situated at a position slightly set back from the distal end portion of the endotracheal tube; more specifically, a position slightly set back from the distal end portion of the endotracheal tube within a position in which an interior wall of the endotracheal tube does not appear the visual field of the endoscope.

Subsequently, the endoscope enters the human body from the mouth along with the endotracheal tube. An operator causes the endoscope to advance or recede while viewing through the eyepiece portion 6. Further, the operator finds the larynx by bending the endoscope or releasing the endoscope from a bent state while gripping the lever 15 of the bending operation mechanism 11. When having found the larynx, the operator causes the endoscope to advance toward the larynx. After having inserted the endoscope into the trachea to a position at which the endotracheal tube does not withdraw readily from the trachea, only the endoscope is removed while the endotracheal tube is left in the trachea. Subsequently, a ventilator is connected to the endotracheal tube, thereby supplying oxygen to the lungs and ensuring breathing of the patient.

At this time, bending of the endoscope is effected in the following manner.

By moving the lever 15 downward, the operator causes the terminal 14 to be pulled toward the eyepiece portion 6.

As a result, the push-pull member 10 is pulled toward the eyepiece portion 6, and the distal end portion of the push-pull member 10 pulls the distal end portion of the elastic member 9 by way of the annular member 12. The elastic member 9 is bent by the pulling force, and consequently the overall bending mechanism 13 consisting of the elastic member 9, the push-pull member 10, and the annular member 12 is bent. As a result of the bending mechanism 13 being bent, the annular member 12 provided at the distal end portion of the bending mechanism 13 is pressed against the interior wall of the plastic tube 8. The plastic tube 8 is bent so as to follow the bend of the bending mechanism 13, thereby bending the endoscope.

At this time, the bending mechanism 13 consisting of the elastic member 9, the push-pull member 10, and the annular member 12 is not fixed by the distal end portion 3 of the insertion section 1 or by the plastic tube 8 and acts as a free end. The pulling force exerted on the push-pull member 10 is not exerted on the distal end portion 3 or on the plastic tube 8. Hence, the insertion section 1 is bent without involvement of a reduction in the length.

In a case where an attempt is made to forcefully restore the endoscope from a bent state by external force; for example, a case where the endoscope bumps into and is pressed against a surrounding wall in spite of the operator's attempt to insert the distal end portion of the endotracheal tube into the trachea by bending the tube while viewing the larynx, the endotracheal tube is restored from a bent state and is straightened. If the endotracheal tube is straightened, the insertion section 1 of the endoscope housed in the endotracheal tube is also straightened along with the endotracheal tube.

Figure 2:
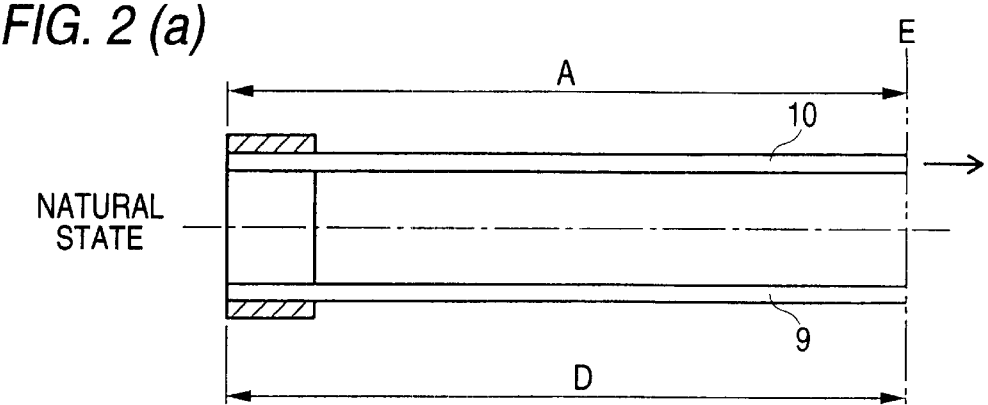
FIGS. 2(a) to (c) descriptive views showing changes in a bending mechanism according to the present embodiment when the bending mechanism is bent.
Figure 2:
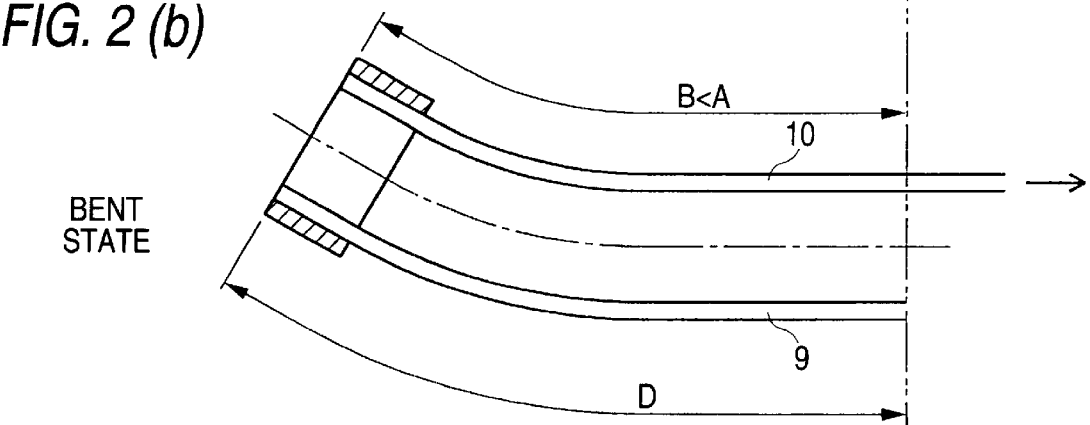
Figure 2:
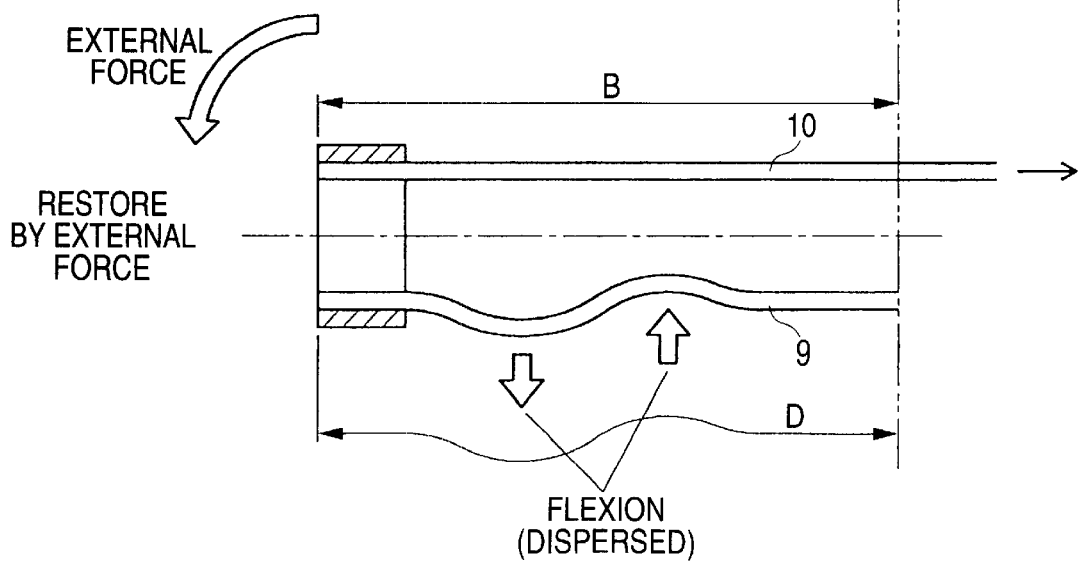
Figure 3:
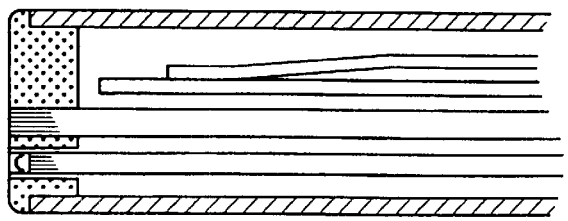
FIGS. 3(a) to (d) descriptive views showing changes in a related-art bending mechanism.
Figure 3:
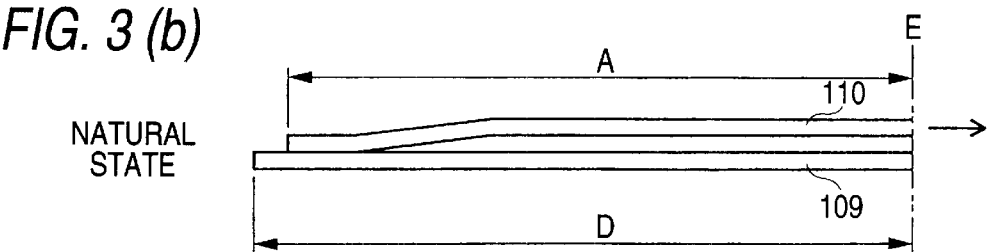
Figure 3:
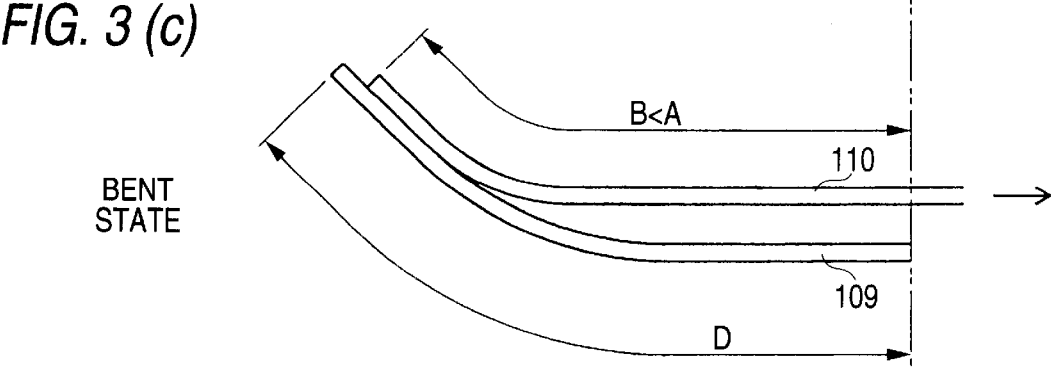
Figure 3:
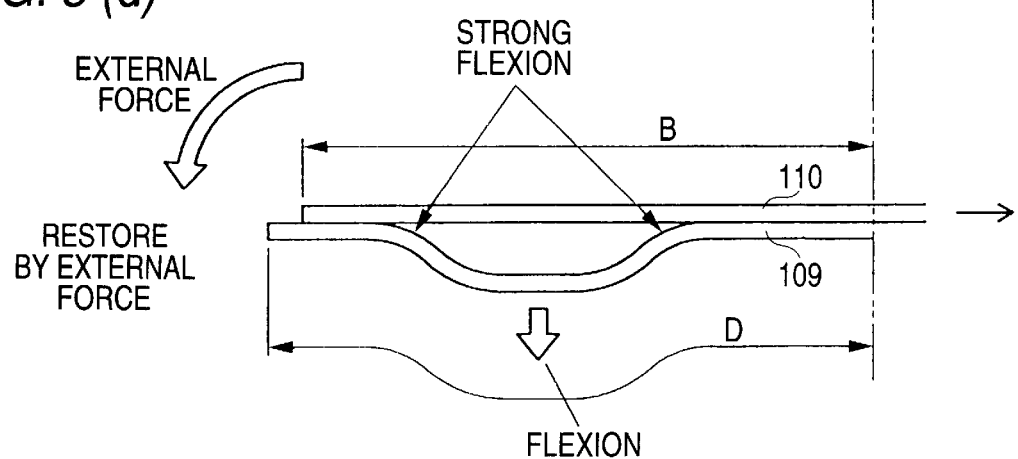

With reference to FIG. 2, changes in the bending mechanism 13 arising in the above-described situation are described.

When the bending mechanism 13 is not bent and remains in a straight state, the elastic member 9 and the push-pull member 10 are set so as to become essentially equal in length. More specifically, provided that the length of the elastic member 9 from its distal end to a reference position E is taken as D, the position E being stationary relatively to the handle operation section, and that the length of the push-pull member 10 from its distal end to the reference position E is taken as A, A and D are set to become essentially equal to each other. When the push-pull member 10 is being pulled and bent, the length of the push-pull member 10 from its distal end to the reference position E becomes B, which is shorter than A. Here, since the proximal end of the elastic member 9 is fixed, the length D of the elastic member 9 remains unchanged. When the bending mechanism 13 is restored from a bent state by external force, the push-pull member 10 is straightened while the length B of the push-pull member 10 from its distal end to the reference position E is retained. As a result, the bending mechanism 13 consisting of the elastic member 9, the push-pull member 10, and the annular member 12 is straightened while the length of the bending mechanism 13 from the distal end to the reference position E is equal to B. Even when the bending mechanism 13 is in a straightened state, the length D of the elastic member 9 from its distal end to the reference position E is still maintained. The bending mechanism 13 is bent by the elastic member 9 absorbing the difference between the lengths B and D. The bending mechanism 13 has no element, such as the push-pull member of the related art structure, which struggles against the elastic member to thereby limit bending of the elastic member 9. Hence, bending is not concentrated on a certain direction and is dispersed and twisted, thereby absorbing the difference in length.

When the bending mechanism 13 usually remains in a bent state, the elastic member 9 is constituted of a sheet. The bending mechanism is bent in the thicknesswise direction of the sheet but is difficult in bending in the widthwise direction of the sheet. Hence, when force is exerted on the distal end portion of the elastic member 9 by the push-pull member 10, the elastic member 9 is stably bent in the thicknesswise direction thereof. The bending action of the elastic member 9 also provides resistance if the insertion section 1 attempts to make a twist. Accordingly, the insertion section 1 is stably bent in a certain direction.

Further, when the push-pull member 10 is formed of a sheet, the effectiveness of resistance is increased.

As has been described in detail, in relation to an endoscope for intubating an endotracheal tube, a distal end portion of a bending mechanism for bending an insertion section is not fixed to a distal end portion of an endoscope insertion section and is taken as a free end. Hence, when the endoscope is bent, force for pulling the bending mechanism does not act to compress the distal end portion of the insertion section. As a result, there can be prevented withdrawal of the distal end portion of the endoscope into an endotracheal tube sheathing the endoscope, which would otherwise arise when the insertion section contracts. Consequently, there can be prevented occurrence of a problem of narrowing of the visual field of the endoscope and limiting exploration of a body cavity, which would otherwise be caused when the endoscope is withdrawn and an interior wall of the endotracheal tube enters the visual field of the endoscope as a result of the endoscope being bent.

As a result of an elastic member of the bending mechanism being formed of a sheet, the elastic member can be bent stably in a certain direction.

Further, as a result of the push-pull member being formed of a sheet or both the elastic member and the push-pull member being formed of sheets, the bending direction of the endoscope can be made further stable.

The distal end portion of the elastic member 9 and the distal end portion of the push-pull member 10 are connected together with a hollow annular member 12, such that the distal end portions oppose each other along a bending direction. The elastic member 9 and the push-pull member 10 are spaced apart from each other. Therefore, even when the endoscope is forcefully restored from a bent state by external force, the elastic member 9 and the push-pull member 10 do not compete with each other, and bending of the elastic member 9 does not concentrate in a certain direction. Hence, there can be obviated a problem of the elastic member 9 being snapped.

Further, the annular member 12 is used for coupling together the distal end portion of the elastic member 9 and the distal end portion of the push-pull member 10. Hence, an image-transmitting fiber bundle 5 and an illumination-light-transmitting fiber bundle 7 can be led to the distal end portion 3 through an inner cavity of the annular member 12, being interposed between the elastic member 9 and the push-pull member 10. Further, the member for coupling together the distal end portion of the elastic member 9 and the distal end portion of the push-pull member 10 is formed into an annular shape identical with the cross section of the insertion section of the endoscope. Accordingly, the inner space of the insertion section of the endoscope can be effectively utilized, thereby obviating a necessity of undesirably increasing the diameter of the insertion section.

What is claimed is:

1. An endoscope for intubating an endotracheal tube comprising:

an elongated insertion section having at least an image-transmitting fiber bundle and an illumination-light-transmitting fiber bundle;

a handle operation section coupled to a proximal end of the insertion section;

a bending operation mechanism provided in the handle operation section; and a bending mechanism for bending the insertion section provided so as to extend from the inside of the insertion section to the bending operation mechanism, the bending mechanism including:

a long elastic member having one end positioned in the vicinity of the distal end portion of the insertion section and the other end fixedly coupled to the proximal end portion of the insertion section or the handle operation section;

a push-pull member having one end positioned in the vicinity of the distal end portion of the insertion section and the other end connected to the bending operation mechanism;

a hollow member for coupling together a distal end portion of the elastic member and a distal end portion of the push-pull member so as to cause the portions to oppose each other along a bending direction, wherein the distal end portion of the elastic member and the distal end portion of the push-pull member, which are coupled together with the hollow member, are provided integrally so as to provide a free end.

2. The endoscope for intubating an endotracheal tube according to claim 1, wherein the elastic member is formed of a sheet.

3. The endoscope for intubating an endotracheal tube according to claim 1, wherein the push-pull member is formed of a sheet.

4. The endoscope for intubating an endotracheal tube according to claim 1, wherein the hollow member is an annular member.

5. The endoscope for intubating an endotracheal tube according to claim 1, wherein the hollow member, the elastic member and the push-pull member are formed integrally within the hollow member.

* * * * *